United States Patent [19]

Belanger et al.

[11] 4,435,579
[45] Mar. 6, 1984

[54] RESOLUTION OF SUBSTITUTED DIBENZO[B,F]THIEPIN-3-CARBOXYLIC ACID-5-OXIDES WITH EPHEDRINE

[75] Inventors: Patrice C. Belanger; Haydn W. R. Williams, both of Dollard des Ormeaux; Joshua Rokach, Chomedey-Laval, all of Canada

[73] Assignee: Merck & Co., Inc., Rahway, N.J.

[21] Appl. No.: 397,253

[22] Filed: Jul. 12, 1982

Related U.S. Application Data

[63] Continuation-in-part of Ser. No. 351,708, Feb. 24, 1982, Pat. No. 4,424,355, which is a continuation of Ser. No. 229,222, Jan. 28, 1981, abandoned.

[51] Int. Cl.³ ........................................... C07D 337/14
[52] U.S. Cl. ..................................................... 549/12
[58] Field of Search ........................................... 549/12

[56] References Cited

U.S. PATENT DOCUMENTS

| | | | |
|---|---|---|---|
| 3,509,154 | 4/1970 | Fouche | 549/12 |
| 4,104,280 | 8/1978 | Ackrell | 549/12 |
| 4,237,160 | 12/1980 | Hamel et al. | 549/12 |
| 4,334,077 | 6/1982 | Belanger et al. | 549/12 |

OTHER PUBLICATIONS

Chemical Abstracts Index Guide, 1977–1981, p. 166 G, "Ephedrine".
Chemical Abstracts Collective Index, 1977–1981, p. 725/CS, "Resolution by [Ephedrine]of . . . ".
Chem. Abstract, 91:190734w.

*Primary Examiner*—Nicky Chan
*Attorney, Agent, or Firm*—Ernest V. Linek; Hesna J. Pfeiffer

[57] ABSTRACT

The present invention is concerned with an improved process for the production of highly active optical isomers of (−) 7 or 8 fluorodibenzo[b,f]thiepin-3-carboxylic acid-5-oxide having the structural formula

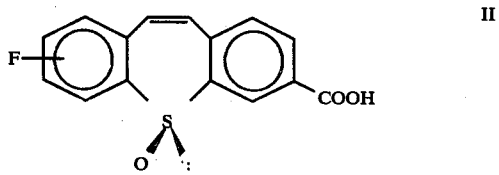

in which the fluoro substituent replaces a hydrogen in the 7 or 8 position. The two active isomers represented by formula II are S(−)7-fluorodibenzo[b,f]thiepin-3-carboxylic acid-5-oxide and R(−)8-fluorodibenzo[b,f]-thiepin-3-carboxylic acid-5-oxide. It is especially concerned with the resolution of the racemic 7 or 8 fluorodibenzo[b,f]thiepin-3-carboxylic acid-5-oxide by first forming and separating diastereomers of said racemic carboxylic acids by salt formation with ephedrine followed by crystallization and regeneration of the desired (−) isomers and recycling of the (+) isomer by racemization of the regenerated isomer. The compounds obtained in high yield by this process are highly active prostaglandin antagonists which are useful in treating a variety of conditions such as allergic asthma.

7 Claims, No Drawings

RESOLUTION OF SUBSTITUTED DIBENZO[B,F]THIEPIN-3-CARBOXYLIC ACID-5-OXIDES WITH EPHEDRINE

RELATIONSHIP TO PRIOR APPLICATIONS

This case is a continuation-in-part of U.S. Ser. No. 351,708, filed Feb. 24, 1982, now U.S. Pat. No. 4,424,355 which in turn was a continuation of U.S. Ser. No. 229,222, filed Jan. 28, 1981, now abandoned.

BACKGROUND OF THE INVENTION

The compounds prepared by the process of the present invention are useful agents for the treatment of conditions such as allergic asthma because of their activity as prostaglandin antagonists. These compounds are disclosed to be present as components of a racemic mixture of compounds of the formula

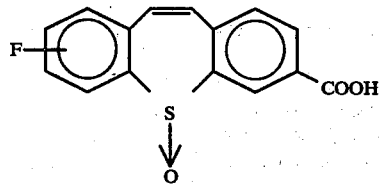

7 or 8 fluorodibenzo[b,f]thiepin-3-carboxylic acid-5-oxide. Both the 7 and 8 fluoro derivatives have unusually high prostaglandin antagonist activity and as disclosed in copending application U.S. Ser. No. 210,082 filed Nov. 24, 1980 of Rokach, Rooney & Cragoe the racemic mixtures can be resolved into (+) and (−) optical isomers in which the bioactivity resides exclusively in the (−) isomer. In the prior application the method of resolution disclosed involves formation of diastereoisomeric amide using an optically active amine, followed by tedious separation of diastereoisomers using fractional crystallization, chromatography and HPLC. In this manner, racemic 7 or 8 fluorodibenzo[b,f]thiepin-3-carboxylic acid-5-oxide of formula I is separated into the biologically active isomers of formula II and the corresponding biologically inactive compounds of formula III pictured structurally hereinbelow

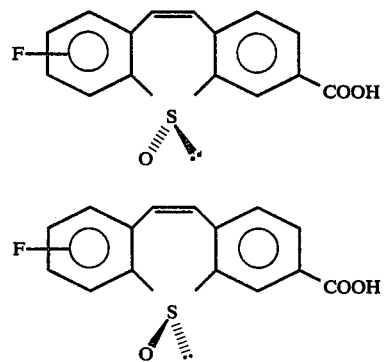

Formula II includes 5(−)7-fluorodibenzo[b,f]thiepin-3-carboxylic acid-S-oxide and R(−)8-fluorodibenzo[b,f]thiepin-3-carboxylic acid-5-oxide. Formula III includes R(+)7-fluorodibenzo[b,f]thiepin-3-carboxylic acid-5-oxide and S(+)8-fluorodibenzo[b,f]-thiepin-3-carboxylic acid-5-oxide.

DESCRIPTION OF THE INVENTION

This application is concerned with an improved process for the preparation of the (−)(7 or 8)-fluorodibenzo[b,f]thiepin-3-carboxylic acid-5-oxides which employs the ephedrine diastereoisomeric salts of the racemic (7 or 8)fluoro-dibenzo[b,f]thiepin-3-carboxylic acid-5-oxide. This process is highly efficient because of the unique solubility properties of the diastereoisomeric salts and the ease of racemization of the (+) or biologically inactive form of the 5-oxide.

In a preferred embodiment of the improved process of resolution, the racemic (7 or 8)fluorodibenzo[b,f]thiepin-3-carboxylic acid-5-oxide is added in equivalent quantity to a solution of d- or l-ephedrine in acetonitrile or in a lower alcohol preferably ethanol and the solution is heated until all solids are dissolved. The ephedrine salt of the (−)(7 or 8)fluorodibenzo[b,f]thiepin-3-carboxylic acid-5-oxide crystallizes from solution in substantially pure form. Further purification may be achieved by recrystallization from methanol. The (−) or bioactive form of the acid is obtained by treatment of the purified ephedrine salt with aqueous acid which regenerates and precipitates the relatively pure enantiomer (−)(7 or 8)fluorodibenzo[b,f]thiepin-3-carboxylic acid-5-oxide. The inactive enantiomer which is present in the mother liquors of the above crystallization is readily converted to the racemic acid by first treating with aqueous acid to hydrolyze the salt and form the (+)(7 or 8)fluorodibenzo[b,f]-thiepin-3-carboxylic acid-5-oxide followed by racemization by treatment with trifluoroacetic anhydride. The racemic acid can be recycled back into the process. The process is applicable in the same manner starting with racemic 7-fluorodibenzo[b,f]thiepin-3-carboxylic acid-5-oxide to produce the desired S(−)7-fluorodibenzo[b,f]thiepin-3-carboxylic acid-5-oxide. Particularly preferred is the use of d-ephedrine to resolve 7-fluorodibenzo[b,f]thiepin-3-carboxylic acid-5-oxide; while l-ephedrine is preferred with the 8-fluorodibenzo[b,f]thiepin-3-carboxylic acid-5-oxide.

EXAMPLE 1

Improved Process Using Ephedrine Salt Method

Step A. Crystallization of the Ephedrine Salt of R(−)-8-Fluorodibenzo[b,f]Thiepin-3-Carboxylic Acid-5-Oxide In a 5 liter flask containing ethanol (3.4 liters) is introduced l-ephedrine (143.2 g.; 0.868 mole). Racemic 8-fluorodibenzo[b,f]thiepin-3-carboxylic acid-5-oxide (250 g.; 0.868 mole) is added rapidly to this solution and brought to reflux. After the addition, the reflux is continued until complete solution is obtained. The resulting solution is then left at room temperature overnight. The crystals are filtered, washed with a small volume of ethanol and air dried to yield the ephedrine salt of the title product having an enantiomeric purity of 93% (134.2 g.; 68%).

Recrystallization from methanol (10 ml. per gram) raises the enantiomeric purity to better than 99% R(−) in a yield of 85%. This salt melts at 211°–213° C. and has an optical rotation of −63±1° (C=1 in methanol).

R(−)-fluorodibenzo[b,f]thiepin-3-carboxylic acid-5-oxide is regenerated from the ephedrine salt by treating with dilute HCl in methanol:water 9:1 9 v:v). It is found to be identical to the product obtained from the brucine salt.

$[\alpha]_D^{25} = -27.7°$ (C=1 in THF).

Step B. Racemization of S(+)8-Fluorodibenzo[b,f]-Thiepin-3-Carboxylic Acid-5-Oxide The mother liquors from the above crystallization, which are predominantly the ephedrine salt of the S(+) acid are acidified and treated with trifluoroacetic anhydride to produce the racemic acid.

The procedure of Example 1 is repeated using the racemic 7-fluorodibenzo[b,f]thiepin-3-carboxylic acid-5-oxide as the starting material in place of the corresponding 8-fluoro compound. In this instance, the d-ephedrine salt of the active S(−)7-fluorodibenzo[b,f]-thiepin-3-carboxylic acid-5-oxide is crystallized directly from the reactive mixture in high yield and the inactive R(+)7-fluorodibenzo[b,f]thiepin-3-carboxylic acid-5-oxide is recovered from the filtrate and reconverted to racemic acid for recycling.

EXAMPLE 2

Crystallization of the d-Ephedrine Salt of S(−)-7-Fluorodibenzo[b,f]Thiepin-3-Carboxylic Acid-5-Oxide In a 5-liter flask containing acetonitrile (3 liters) are introduced d-ephedrine (82.6 g, 0.50 mole) and racemic 7-fluorodibenzo[b,f]thiepin-3-carboxylic acid-5-oxide (141 grams, 0.49 mole) and the mixture is brought to reflux. The reflux is continued until solution has occurred. The resulting solution is filtered hot and the filtrate is left at room temperature overnight. The supernatant is decanted and the crystals redissolved in a 1 liter of boiling acetonitrile. The product from this second crystallization (39 grams) mp: 174°–177° shows an enantiomeric purity of 96%. The free acid is liberated from the salt as in Example 1 and after recrystallization from isopropanol alcohol there is obtained 13.6 grams of the S-(−) acid in an optical purity $\geq 99.5\%$.

$[\alpha]_{RT}^D = -20.1°$ [C=1 in 5% aqueous NaHCO₃-/EtOH (2:1)]

mp: dec. 256° resolidifies and melts 310°–316° C.
The residues enriched in the unwanted R-isomer can be racemized as in Example 1, Step B.

What is claimed is:

1. An improved process for the preparation of (−)(7 or 8)-fluorodibenzo[b,f]thiepin-3-carboxylic acid-5-oxide of the Formula I:

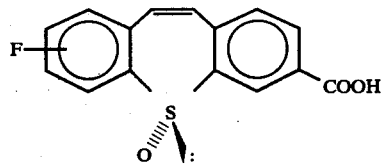

which comprises:
   (1) Heating a solution of equimolar amounts of racemic (7 or 8)-fluorodibenzo[b,f]thiepin-3-carboxylic acid-5-oxide and (d or l)-ephedrine in a lower alcohol to form a diastereoisomeric mixture of (d or l)-ephedrine salts of (−)(7 or 8)-fluorodibenzo[b,f]-thiepin-3-carboxylic acid-5-oxide and (+)(7 or 8)-fluorodibenzo[b,f]thiepin-3-carboxylic acid-5-oxide;
   (2) Recovering the crystalline (d or l)-ephedrine (−) acid salt;
   (3) Recycling the (d or l)-ephedrine (+) acid salt by first hydrolysis with aqueous acid followed by racemization with trifluoroacetic anhydride to regenerate the racemic (7 or 8)-fluorodibenzo[b,f]-thiepin-3-carboxylic acid-5-oxide; and
   (4) Acidifying said (d or l)-ephedrine (−) acid salt with aqueous acid to produce (−)(7 or 8)-fluorodibenzo[b,f]thiepin-3-carboxylic acid-5-oxide.

2. The process of claim 1 wherein the formation of the diasterioisomeric mixture of ephedrine salts is carried out in the presence of acetonitrile or a lower aliphatic alcohol selected from methanol, ethanol, propanol, i-propanol or mixture thereof.

3. The d- or l-ephedrine salt of racemic (7 or 8)-fluorodibenzo[b,f]thiepin-3-carboxylic acid-5-oxide.

4. The d- or l-ephedrine salt of R(−)8-fluorodibenzo[b,f]thiepin-3-carboxylic acid-5-oxide of claim 3.

5. The d- or l-ephedrine salt of S(+)8-fluorodibenzo[b,f]thiepin-3-carboxylic acid-5-oxide of claim 3.

6. The d- or l-ephedrine salt of S(−)7-fluorodibenzo[b,f]thiepin-3-carboxylic acid-5-oxide of claim 3.

7. The d- or l-ephedrine salt of R(+)7-fluorodibenzo[b,f]-thiepin-3-carboxylic acid-5-oxide of claim 3.

* * * * *